United States Patent [19]
Piomelli et al.

[11] Patent Number: 5,925,672
[45] Date of Patent: Jul. 20, 1999

[54] METHODS OF TREATING MENTAL DISEASES, INFLAMMATION AND PAIN

[75] Inventors: Daniele Piomelli; Massimiliano Beltramo, both of San Diego, Calif.

[73] Assignee: Neurosciences Research Foundation, Inc., San Diego, Calif.

[21] Appl. No.: 08/764,104

[22] Filed: Dec. 6, 1996

[51] Int. Cl.$^6$ .......................... A61K 31/34; A61K 31/35
[52] U.S. Cl. .......................... 514/460; 514/473; 514/336
[58] Field of Search .................................. 514/460, 473, 514/336

[56] References Cited

U.S. PATENT DOCUMENTS

| | | | |
|---|---|---|---|
| 4,602,006 | 7/1986 | Krantz et al. | 514/473 |
| 5,001,242 | 3/1991 | Kuekenhoehner et al. | 549/356 |
| 5,208,244 | 5/1993 | Weiss et al. | 514/460 |
| 5,286,746 | 2/1994 | Poss | 514/460 |
| 5,294,724 | 3/1994 | Jendralla et al. | 549/292 |
| 5,308,864 | 5/1994 | Lewis et al. | 514/460 |
| 5,385,932 | 1/1995 | Vickers | 514/460 |
| 5,447,957 | 9/1995 | Adams et al. | 514/564 |
| 5,470,882 | 11/1995 | Dixon et al. | 514/596 |

OTHER PUBLICATIONS

Hazen et al., *Suicide Inhibition of Canine Myocardial Cytosolic Calcium–independent Phospholipase A$_2$*, Journal of Biological Chemistry, The, Col. 266, No. 11, pp. 7227–7232 (Apr. 15, 1991).

Fontana et al., *Analysis of Anandamide, an Endogenous Cannabinoid Substance, and of Other Natural N–Acylethanolamines*, Prostaglandins Leukotrienes and Essential Fatty Acids, 53, pp. 301–308 (1995).

Desarnaud et al., *Anandamide Amidohydrolase Activity in Rat Brain Microsomes*, The Journal of Biological Chemistry, vol. 270, No. 11, pp. 6030–6035 (Mar. 17, 1995).

Beltramo et al., *Inhibition of anandamide hydrolysis in rat brain tissue by (E)–6–(bromomethylene) tetrahydro–3–(1–naphthalenyl)–2H–pyran–2–one*, FEBS Letters 403, pp. 263–267 (1997).

Cadas et al., *Biosynthesis of an Endogenous Cannabinoid Precursor in Neurons and its Control by Calcium and cAMP*, The Journal of Neuroscience, 16(12):3934–3942 (Jun. 15, 1996).

Remington, *Pharmaceutical Sciences*, Arthur Osol. Ed., 16th Ed., Mack Publishing Co. (1980).

Chemical Abstracts AN 1996:403231, Mallet et al, Jan. 1996.

*Primary Examiner*—Keith D. MacMillan
*Attorney, Agent, or Firm*—McDermott Will & Emery

[57] ABSTRACT

Methods are disclosed for treating or preventing disorders such as mental diseases, inflammation and pain by inhibiting the enzyme anandamide amidohydrolase. A therapeutically effective level of an anandamide amidohydrolase inhibitor is administered such as a therapeutically effective level of a haloenol lactone. Preferably, the haloenol lactone is of the formula:

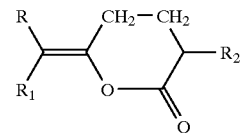

wherein R is hydrogen, $R_1$ is a halogen, and $R_2$ is selected from the group consisting of aryl, aryloxy, and heteroaryl radicals, derivatives of said haloenol lactones, and mixtures thereof. The haloenol lactone, E-6-(bromomethylene) tetrahydro-3-(1-naphthalenyl)-2H-pyrane-2-one, is most preferred.

2 Claims, 2 Drawing Sheets

METHODS OF TREATING MENTAL DISEASES, INFLAMMATION AND PAIN

FIELD OF THE INVENTION

The invention relates to methods and compositions for treating disorders such as mental diseases, inflammation and pain. More particularly, the invention relates to methods for treating such disorders by administering a therapeutically effective level of an anandamide amidohydrolase inhibitor.

BACKGROUND OF THE INVENTION

Anandamide (N-arachidonoylethanolamine) is thought to act as an endogenous cannabinoid neurotransmitter in vertebrate nervous systems. It binds to and activates cannabinoid receptors and simulates many distinctive effects typical of plant-derived or synthetic cannabinoid drugs.

Biochemical evidence indicates that anandamide is produced in and released from neurons in an activity-dependent manner. Further, as expected of a signalling molecule, anandamide is short-lived: its life-span is limited by uptake into neural cells and by enzymatic hydrolysis. Anandamide hydrolysis is catalyzed by the enzyme anandamide amidohydrolase, which converts anandamide to yield two inactive metabolites, arachidonate and ethanolamine. This reaction is illustrated by the following:

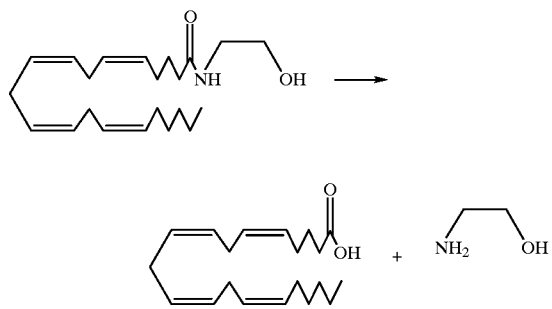

Anandamide amidohydrolase is likely to play an important role in the physiological degradation of anandamide. Three lines of evidence support this possibility. First, anandamide amidohydrolase is highly selective. Second, anandamide amidohydrolase is discretely distributed in the central nervous system, where its localization parallels that of cannabinoid receptors. Third, a protease inhibitor that blocks anandamide amidohydrolase non-selectively, phenylmethylsulphonylfluoride, extends the actions of anandamide.

Therefore, inhibition of anandamide amidohydrolase to increase the accumulation of anandamide at its sites of action is desirable as a potential therapeutic approach for the treatment or prevention of disorders such as mental diseases, inflammation and pain, including treatment or prevention of schizophrenia, mood disorders, anorexia, multiple sclerosis, spasticity and glaucoma. Despite these potential applications, no potent and selective inhibitors of anandamide amidohydrolase have been identified as yet.

The anandamide amidohydrolase inhibitors useful in the present invention comprise haloenol lactones. The preferred haloenol lactones are compounds of the formula:

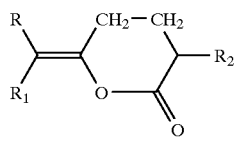

wherein R is hydrogen, $R_1$ is a halogen, and $R_2$ is selected from the group consisting of aryl, aryloxy, and heteroaryl radicals. A most preferred haloenol lactone is E-6-(bromomethylene) tetrahydro-3-(1-naphthalenyl)-2H-pyrane-2-one which has the following formula:

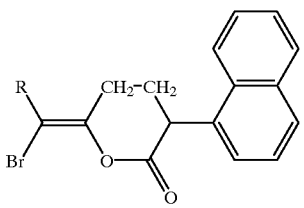

The synthesis of this compound and the identification of its ability to inhibit an enzyme which is unrelated to anandamide amidohydrolase, i.e., the cardiac calcium-independent phospholipase $A_2$, have been described in the following patents and publications: Hazen, et al., *J. Biol. Chem.* 266, 7227–7232 (1991); Weiss, et al., U.S. Pat. No. 5,208,244; and Balsinde, et al., *Proc. Natl. Acad. Sci. U.S.A.* 92, 8527–8531 (1995).

SUMMARY OF THE INVENTION

The invention comprises methods of treating or preventing disorders such as mental diseases, inflammation and pain, including schizophrenia, mood disorders, anorexia, multiple sclerosis, spasticity and glaucoma by administering a therapeutically effective level of an anandamide amidohydrolase inhibitor. The preferred anandamide amidohydrolase inhibitors comprise haloenol lactones. The preferred haloenol lactones are compounds of the formula:

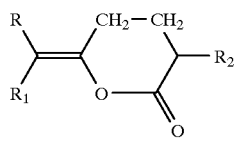

wherein R is hydrogen, $R_1$ is a halogen, and $R_2$ is selected from the group consisting of aryl, aryloxy, and heteroaryl radicals, and derivatives and mixtures thereof. The most preferred anandamide amidohydrolase inhibitors comprise E-6-(bromomethylene)tetrahydro-3-(1-naphthalenyl)-2H-pyrane-2-one, derivatives of this compound, and mixtures thereof.

The present invention further comprises methods of inhibiting anandamide amidohydrolase by administering a therapeutically effective amount of a haloenol lactone. The preferred haloenol lactones are compounds of the formula:

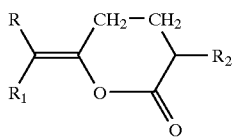

wherein R is hydrogen, $R_1$ is a halogen, and $R_2$ is selected from the group consisting of aryl, aryloxy, and heteroaryl radicals, derivatives of these compounds and mixtures thereof. The most preferred anandamide amidohydrolase inhibitors comprise E-6-(bromomethylene)tetrahydro-3-(1-naphthalenyl)-2H-pyrane-2-one.

The invention further comprises pharmaceutical compositions comprising anandamide amidohydrolase inhibitors for treating mental diseases, inflammation and pain, such as schizophrenia, mood disorders, anorexia, multiple sclerosis, spasticity and glaucoma. The preferred compositions comprise a haloenol lactone at a therapeutically effective level to inhibit anandamide amidohydrolase.

DETAILED DESCRIPTION OF THE INVENTION

The preferred anandamide amidohydrolase inhibitors of the invention are haloenol lactones. The preferred haloenol lactones are compounds of the general formula:

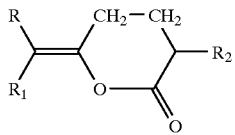

wherein R is hydrogen, $R_1$ is a halogen, and $R_2$ is selected from the group consisting of aryl, aryloxy, and heteroaryl radicals, and derivatives and mixtures thereof. The preferred haloenol lactones useful in the methods and compositions of the invention include E-6-(bromomethylene)tetrahydro-3-(1-naphthalenyl)-2H-pyrane-2-one, derivatives of this compound, and mixtures thereof.

Inhibition of anandamide amidohydrolase causes the accumulation of endogenously produced anandamide. Endogenous anandamide, in turn, activates cannabinoid receptors, resulting in therapeutically favorable effects that include mood elevation, appetite stimulation, relief of pain and inflammation, and symptomatic relief in diseases such as multiple sclerosis and glaucoma.

The following examples illustrate the anandamide amidohydrolase inhibitors of the invention.

EXAMPLE 1

Anandamide amidohydrolase assay

An assay was developed which demonstrated inhibition of rat brain anandamide amidohydrolase by E-6-(bromomethylene) tetrahydro-3-(1-naphthalenyl)-2H-pyrane-2-one. This assay consisted of determining the amount of radiolabeled arachidonic acid liberated from radiolabeled anandamide by rat brain anandamide amidohydrolase in the presence of various concentrations of E-6-(bromomethylene)tetrahydro-3-(1-naphthalenyl)-2H-pyrane-2-one. This assay was also used to show that E-6-(bromomethylene)tetrahydro-3-(1-naphthalenyl)-2H-pyrane-2-one is more effective on brain tissue anandamide amidohydrolase activity, by examining its effect on rat liver anandamide amidohydrolase.

Anandamide amidohydrolase was measured in rat brain or rat liver microsome fractions. The fractions (0.1 mg of protein) were prepared following the protocols of Desarnaud et al., *J. Biol. Chem.* 270, 6030–6035 (1995), and were incubated in 50 mM Tris-Cl (pH 7.4) at 37° C., in the presence of radiolabeled anandamide obtained from New England Nuclear, Wilmington, Del., 221 Ci/mmol), plus various concentrations of test inhibitor (0.1–100 $\mu$M). After 10 min. of incubation, the reactions were stopped with cold methanol, the radiolabeled lipids extracted with chloroform, and the organic phases brought to dryness under a stream of $N_2$ gas. The radioactive products were then fractionated by thin-layer chromatography (solvent system: chloroform/methanol/ammonia, 90:10:1 vol/vol/vol), collected by scraping appropriate areas of the chromatography plate, and quantified by liquid scintillation counting.

Figure 1:
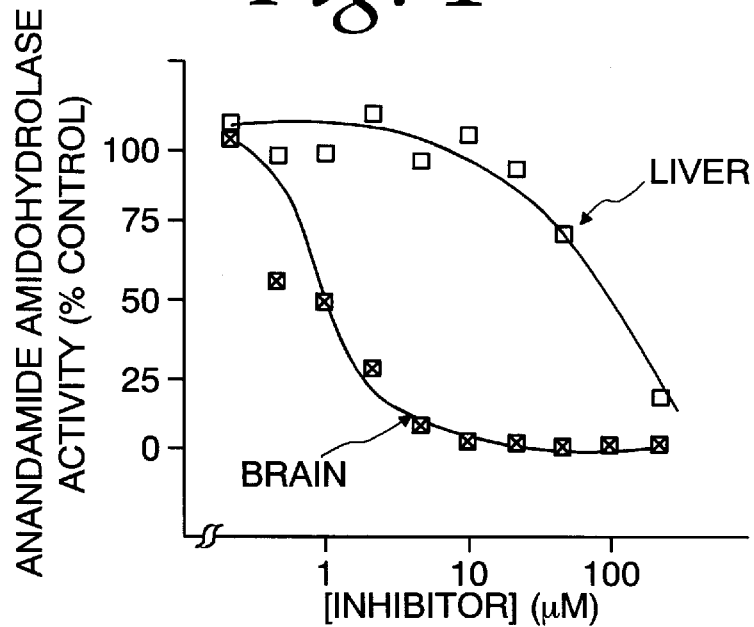
FIG. 1 is a graph showing a comparison of the effects of a haloenol lactone of the invention on anandamide amidohydrolase activities from rat brain and rat liver.

The effects of E-6-(bromomethylene)tetrahydro-3-(1-naphthalenyl)-2H-pyrane-2-one on anandamide amidohydrolases from rat brain or liver are shown in FIG. 1. This compound is potent in inhibiting brain anandamide amidohydrolase. The concentration of E-6-(bromomethylene) tetrahydro-3-(1-naphthalenyl)-2H-pyrane-2-one which decreases the enzyme activity to 50% of the activity measured in the absence of the compound (defined as $IC_{50}$), was 0.7 $\mu$M.

Underscoring the tissue differences of this inhibitory effect, inhibition of the liver enzyme was achieved at concentrations of E-6-(bromomethylene)tetrahydro-3-(1-naphthalenyl)-2H-pyrane-2-one that were more than 100-fold higher than in brain ($IC_{50}$=97 $\mu$M).

Pharmaceutical compositions comprising the haloenol lactones of the invention can be administered utilizing an effective inhibitory amount of the compound(s). This amount can range from about 1 nM to 0.1 mM, preferably from about 1 $\mu$M to about 50 $\mu$M. A most preferred effective amount is about 10 $\mu$M. Such compositions can be prepared with acceptable diluents and/or carriers, as described, for example, in Remington's *Pharmaceutical Sciences*, Arthur Osol, Ed., 16th Ed., 1980, Mack Publishing Company.

EXAMPLE 2

Assay in cultures of cortical astrocytes

An additional assay demonstrated inhibition of anandamide amidohydrolase in intact neural cells. This assay consisted of determining the amount of radiolabeled arachidonic acid produced, when cultures of rat cortical astrocytes were incubated in the presence of radiolabeled anandamide.

Cultures of rat cortical astrocytes, essentially free of neurons, were prepared following the standard procedures described in Cadas et al., *J. Neurosci.* 16, 3934–3942 (1996), and used after 3 weeks in culture. The cultures were incubated in Krebs Tris solution (pH 7.4) at 37° C., in the presence of radiolabeled anandamide plus various concentrations of E-6-(bromomethylene)tetrahydro-3-(1- naphthalenyl)-2H-pyrane-2-one (0.1–100 μM). After 20 min. of incubation, the reactions were stopped with cold methanol, and the cells were scraped from the culture dishes and subjected to chloroform extraction. The organic phases were dried, and analyzed as follows. To measure radiolabeled anandamide and arachidonic acid, the organic extracts were fractionated by silica gel G column chromatography, as described in Fontana et al., *Prostaglandins Leukotrienes Essential Fatty Acids* 53, 301–308 (1995). Radiolabeled anandamide and arachidonic acid were eluted from the column with a solvent system of chloroform/methanol (9:1, vol/vol), and further purified by thin-layer chromatography (solvent system of chloroform/methanol/ammonia, 80:20:1, vol/vol/vol). To measure radiolabeled phospholipids, which were formed in intact cells from the enzymatic esterification of radiolabeled arachidonic acid, the organic extracts were fractionated by thin-layer chromatography (solvent system of chloroform/methanol/ammonia/water, 65:25:4:1, vol/vol/vol/vol).

Figure 2A:
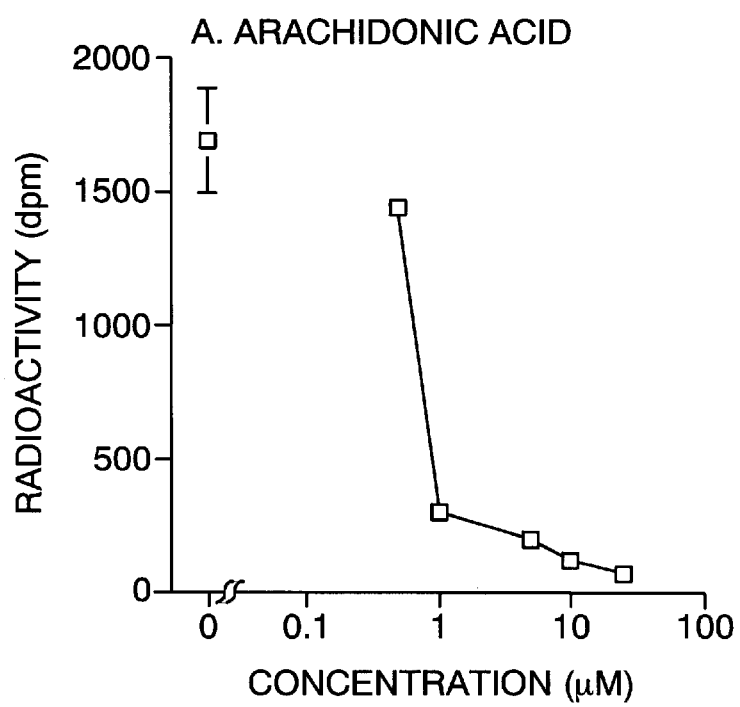
FIGS. 2A and 2B are graphs showing measurements of the levels of radiolabeled arachidonic acid accumulated in the presence of various concentrations of a haloenol lactone of the invention (FIG. 2A), or levels of phospholipids containing radiolabeled arachidonic acid (FIG. 2B)
Figure 2B:
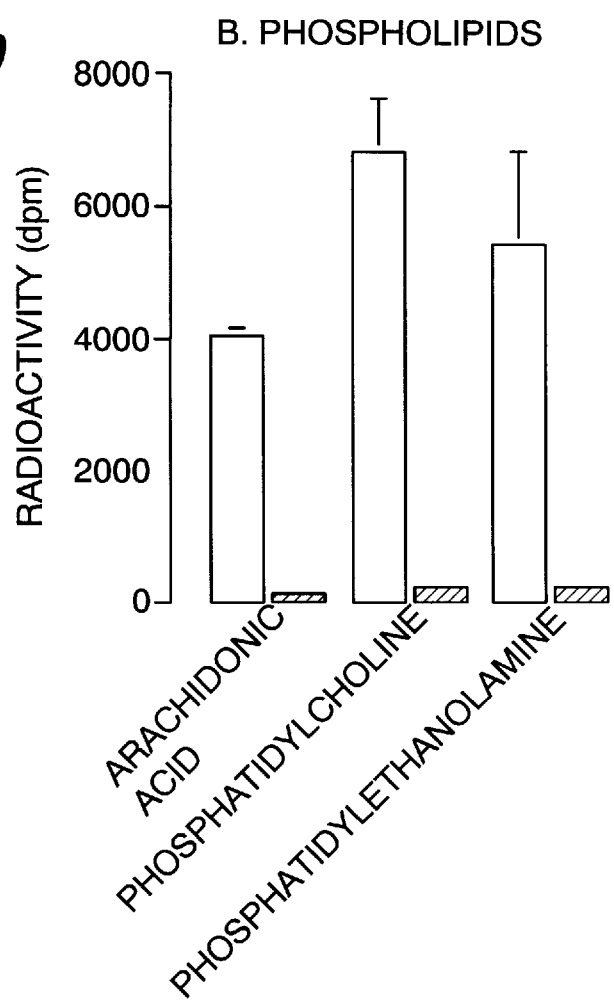
Figure 3:
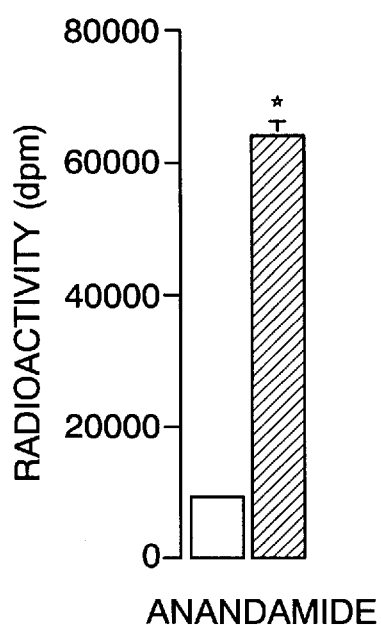
FIG. 3 is a graph showing that intracellular levels of radiolabeled anandamide were greatly increased in the presence of a haloenol lactone of the invention.

E-6-(bromomethylene)tetrahydro-3-(1-naphthalenyl)-2H-pyrane-2-one is potent in inhibiting the anandamide amidohydrolase of intact astrocytes ($IC_{50}$=0.5 uM). This can be shown either by measuring the levels of radiolabeled arachidonic acid accumulated in the presence of various concentrations of the inhibitor (FIG. 2A), or by measuring the levels of phospholipids containing radiolabeled arachidonic acid (FIG. 2B). By contrast, E-6-(bromomethylene)tetrahydro-3-(1-naphthalenyl)-2H-pyrane-2-one does not inhibit the uptake of radiolabeled anandamide. This is indicated by the fact that the intracellular levels of radiolabeled anandamide were greatly increased in the presence of this compound, which would not be expected if the uptake were inhibited (FIG. 3).

The embodiments of the invention disclosed herein have been discussed for the purpose of familiarizing the reader with novel aspects of the invention. Although preferred embodiments of the invention have been shown and described, many changes, modifications, and substitutions may be made by one having skill in the art without necessarily departing from the spirit and scope of the invention.

We claim:

1. A method of treating mental disease, inflammation or pain comprising administering a therapeutically effective level of an anandamide amidohydrolase inhibitor wherein said inhibitor is a haloenol lactone which is represented by the following structural formula:

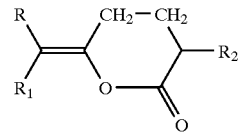

wherein R is hydrogen, $R_1$ is a halogen and $R_2$ is selected from the group consisting of aryl and aryloxy and mixtures thereof.

2. The method of claim 1 wherein the haloenol lactone comprises E-6-(bromomethylene)tetrahydro-3-(1-naphthalenyl)-2H-pyrane-2-one.

* * * * *